(12) United States Patent
Holloway

(10) Patent No.: US 7,196,338 B2
(45) Date of Patent: Mar. 27, 2007

(54) ULTRA-THIN SAMPLE PREPARATION FOR TRANSMISSION ELECTRON MICROSCOPY

(75) Inventor: Nathan V. Holloway, Mesquite, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 11/094,443

(22) Filed: Mar. 31, 2005

(65) Prior Publication Data
US 2006/0226363 A1    Oct. 12, 2006

(51) Int. Cl.
*G21K 7/00*    (2006.01)

(52) U.S. Cl. .................. 250/440.11; 250/307; 250/304; 250/311; 438/14; 438/22; 216/2

(58) Field of Classification Search ............. None
See application file for complete search history.

(56) References Cited

U.S. PATENT DOCUMENTS

| 6,194,720 B1 * | 2/2001 | Li et al. ............ 250/311 |
| 6,576,900 B2 * | 6/2003 | Kelly et al. ......... 250/307 |
| 2006/0065830 A1 * | 3/2006 | Bauer et al. ........ 250/307 |

* cited by examiner

*Primary Examiner*—Jack Berman
*Assistant Examiner*—Zia R. Hashmi
(74) *Attorney, Agent, or Firm*—Peter K. McLarty; W. James Brady III; Frederick J. Telecky, Jr.

(57) ABSTRACT

In accordance with the invention, there is a method of fabricating a material for transmission electron microscopy comprising removing a first portion from a material having a thickness of ($d_1$) to form a thinned material having a thickness of ($d_2$), contacting the thinned material to a sacrificial layer having a thickness of ($s_1$), and removing a second portion from the thinned material so the thinned material has a thickness of ($d_3$), wherein ($d_3$)<($d_2$).

23 Claims, 1 Drawing Sheet

ULTRA-THIN SAMPLE PREPARATION FOR TRANSMISSION ELECTRON MICROSCOPY

FIELD OF THE INVENTION

The subject matter of this invention relates to methods of fabricating a material for inspection. More particularly, the subject matter of the present invention relates to fabricating a material for Transmission Electron Microscopy (TEM) using Focused Ion Beam (FIB).

BACKGROUND OF THE INVENTION

Transmission Electron Microscopy (TEM) is a method of analyzing extremely small features of a material, typically 0.5 nm to about 100 nm. TEM generally monitors electrons as they are transmitted through a thin material. As such, thinner materials can provide better TEM images than thicker materials. This is because electrons can transmit more easily through the thin material.

TEM is often used in the semiconductor industry. For example, TEM can be used to determine whether the features formed on a device conform to design specifications. For proper TEM analysis, a region of the material having a feature of interest should be made thinner than the feature of interest. This is because when the material thickness exceeds the feature size, the data obtained by TEM may be misinterpreted, distorted, or may show the superposition of multiple features. All of these issues can result in an unacceptable TEM analysis. Thus, there is a need to thin the material as much as possible. However, as the critical dimensions in the semiconductor industry continue to scale down, it is becoming increasingly more difficult to sufficiently thin materials for TEM.

Conventional TEM sample preparation removes a thin portion of material from a bulk material. This is typically done using FIB. The FIB uses a beam of ions, such as a beam of gallium ions, to cut the thin material from the bulk. Currently, an experienced FIB user is able to cut a sample to have a minimum thickness of 500 Å without causing too much amorphization of the sample. However, various features on state of the art semiconductor devices can be smaller than this minimum thickness, and, as stated above, this can result in analysis errors.

Some problems that limit the preparation of thinner materials using FIB include poor mechanical stability of the material and poor thermal transport during FIB and amorphization of the surface. As such, it has not been possible to produce a material thinned to a sufficient degree so as to allow accurate analysis.

Accordingly, the present invention solves these and other problems of the prior art when forming thinned material that can provide accurate TEM analysis.

SUMMARY OF THE INVENTION

In accordance with the invention, there is a method of fabricating a material for transmission electron microscopy comprising removing a first portion from a material having a thickness of $(d_1)$ to form a thinned material having a thickness of $(d_2)$, contacting the thinned material to a sacrificial layer having a thickness of $(s_1)$, and removing a second portion from the thinned material so the thinned material has a thickness of $(d_3)$, wherein $(d_3)<(d_2)$.

According to another embodiment, there is a method of fabricating a thinned material for site specific transmission electron microscopy, comprising removing a first portion of a first side of a material, contacting the first side to a sacrificial layer, wherein the sacrificial layer has a thickness of $(s_1)$, and removing a second portion from a second side of the material. The method also comprises removing a portion of the sacrificial layer to a thickness of $(s_2)$, wherein: $0 \leq (s_2) \leq (s_1)$.

According to another embodiment, there is a structure for inspection using transmission electron microscopy, comprising a sample material having a thickness of less than about 450 Å and a sacrificial layer contacting the sample material.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Figure 1:
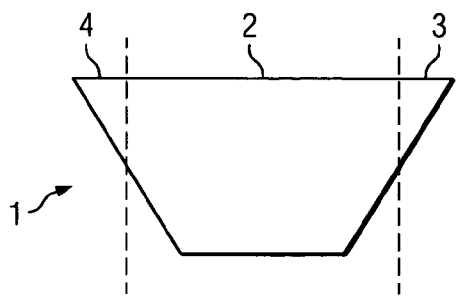
FIG. 1 is a fragmentary cross-sectional diagram of a conventional sample for TEM analysis.
Figure 2A:
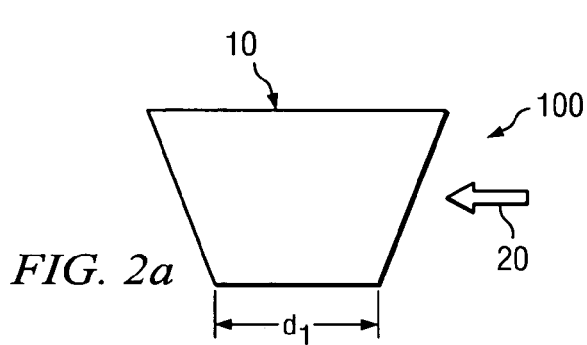
FIGS. 2A–2F are fragmentary cross-sectional diagrams illustrating various steps in forming a sample for TEM analysis in accordance with various embodiments of the present invention.

According to various embodiments there is a method of fabricating a sample, also called a thinned material, for Transmission Electron Microscopy (TEM). An exemplary process 100 is shown, for example, in FIGS. 2A–2F. FIG. 2A depicts a material 10 having an arbitrary shape. According to various embodiments, material 10 can comprise a semiconductor device or a portion of a semiconductor device. For example, material 10 can comprise a metal, semiconductor, insulator, or combinations thereof. It is to be understood that material 10 can comprise any bulk material that a use intends to characterize. According to various embodiments, material 10 can be a section that has been removed from a large piece of material. While material 10 in FIG. 2A is shown to have a generally trapezoidal shape, material 10 can be any shape. Further, for ease of description, the shapes shown herein are drawn to be two-dimensional objects.

According to various embodiments, a region of material 10 can have a first thickness $(d_1)$. Typically, first thickness ($d_1$) can represent the thinnest region of material 10. According to various embodiments, a first removal technique 20 can be used to remove a first portion of material 10. Various removal techniques, as are known to one of ordinary skill in the art, can be used to remove the first portion of material 10. Exemplary removal techniques can include Focused Ion Beam (FIB), ion milling, wet etching, dry etching, and chemical etching. Further, combinations of the various removal techniques can be used or one removal technique can be used to remove the first portion from material 10.

Figure 2B:
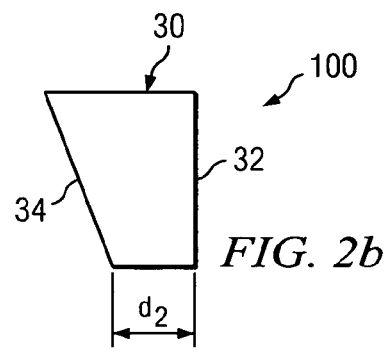

As a result of first removal technique 20, material 10 can be thinned and can be referred to as a thinned material 30 as shown in FIG. 2B. Thinned material 30 generally comprises at least a first side 32 and a second side 34. FIG. 2B shows first side 32 has been thinned generally opposite second side 34. However, this need not necessarily be so. At this point, thinned material 30 has been thinned to have a second thickness ($d_2$) that is less than thickness ($d_1$). According to various embodiments, thickness ($d_2$) can be about 80% or less than thickness ($d_1$). For example, thickness ($d_2$) can be about 500 Å or greater.

Figure 2C:
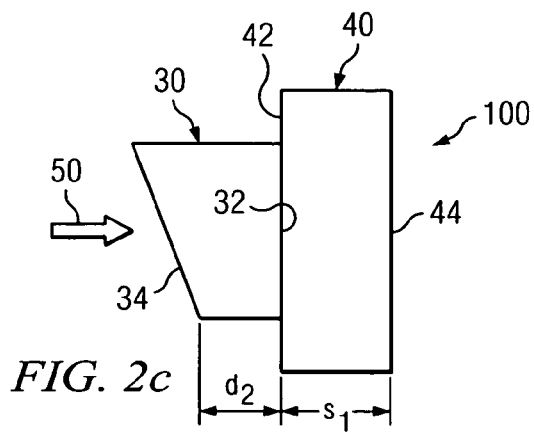

As shown in FIG. 2C, thinned material 30 can be contacted to a sacrificial layer 40. For example, first side 32 of thinned material 30 can contact a first side 42 of sacrificial layer 40. As will be understood, sacrificial layer 40 can also comprise a second side 44 opposite first side 42. As shown in FIG. 2C, a region of sacrificial layer 40 can have a first layer thickness ($s_1$). Typically, first layer thickness ($s_1$) can represent the thinnest region of sacrificial layer 40 and can be understood to be between first side 42 and second side 44.

According to various embodiments, a second material removal technique 50 can be used to remove a second portion of thinned material 30. Various removal techniques can be used to remove the second portion of thinned material 30. Exemplary removal techniques can include dry etching and/or wet etching, including ion milling and FIB. Further, combinations of various removal techniques, known to one of ordinary skill in the art, can be used or one removal technique can be used. Second removal technique 50 can be used to further thin thinned material 30. According to various embodiments, second removal technique can be applied to second material side 34.

According to various embodiments, sacrificial layer 40 can comprise a single layer. Further, sacrificial layer 40 can comprise various materials, such as a metal, a semiconductor, or an insulator. For example, sacrificial layer 40 can comprise an oxide, a nitride, carbide, or a metal. Still further, sacrificial layer 40 can comprise silicon oxide, aluminum oxide, TEOS, silicon nitride, aluminum nitride, silicon carbide, aluminum, platinum, copper, or glue. However, sacrificial layer 40 can comprise other materials.

According to various embodiments, thinned material 30 can contact sacrificial layer 40 in various ways. As used herein, contacted is understood to mean physically touching, including bonded to, with or without an adhesive material, and placed next to. For example, sacrificial layer 40 can contact thinned material 30 by a glue, an adhesive, or other bonding technique. Moreover, according to various embodiments, sacrificial layer 40 can be sputter deposited or epitaxially grown on thinned material 30.

According to various embodiments, sacrificial layer 40 thickness ($s_1$) can be from about 20 Å to about 5000 Å. According to other embodiments, thickness ($s_1$) can be about 500 Å to about 1000 Å, and in other embodiments, thickness ($s_1$) can be at least about 500 Å.

According to various embodiments, sacrificial layer 40 can comprise at least two layers. For example, sacrificial layer 40 can comprise two, three, four, or more layers. According to various embodiments, each of the layers comprising sacrificial layer 40 can be similar in composition, thickness, method of formation, etc.; and some of the layers comprising sacrificial layer 40 can be similar and some can be dissimilar from each other in composition, thickness, method of formation, etc.; or each of the layers comprising sacrificial layer 40 can be different from each other in composition, thickness, method of formation, etc. However, it will be understood that the layers comprising sacrificial layer 40 can contact each other so as to make up sacrificial layer 40. Moreover, the layers comprising sacrificial layer 40 can form thickness ($s_1$).

Figure 2D:
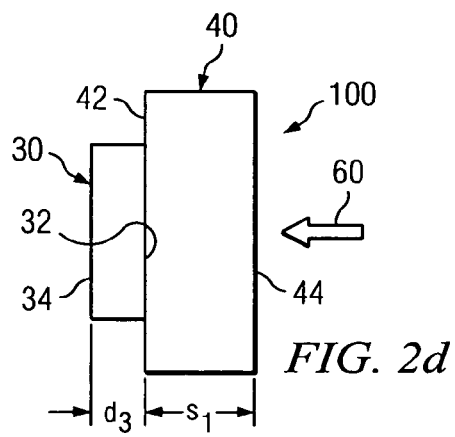

As a result of second removal technique 50, thinned material 30 has a thickness ($d_3$), as shown in FIG. 2D. At this point, thickness ($d_3$) can be about 80% or less than thickness ($d_2$). According to various embodiments, thickness ($d_3$) can be about 50 Å to about 1000 Å.

According to various embodiments, material 10 can contact sacrificial layer 40 without having had the first portion removed. For example, material 10 can have a thickness that does not require the first removal technique. In this case, material 10 will be understood to have thickness ($d_2$) and contacts sacrificial layer 40.

According to various embodiments, a third removal technique 60 can be used to remove a portion of sacrificial layer 40. Various removal techniques known to one of ordinary skill in the art can be used to remove the portion from sacrificial layer 40. Exemplary techniques can include FIB, ion milling, wet etching, dry etching, and chemical etching. Further combinations of various removal techniques can be used, or one removal technique can be used. According to various embodiments, the portion can be removed from second side 44 of sacrificial layer 40.

Figure 2E:
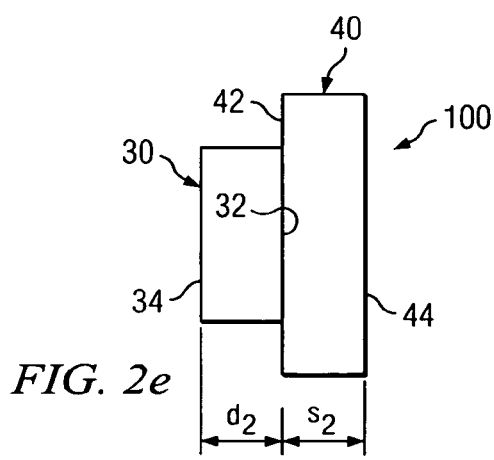

As a result of third removal technique 60, sacrificial layer 40 has a thickness ($s_2$), as shown in FIG. 2E. At this point, thickness ($s_2$) can be about 80% or less than thickness ($s_1$). For example, ($s_2$) can be about 0 to about 1000 Å, dependent on the desired results. Moreover, in various embodiments, thickness ($s_2$) can be from 0 to 100% of the original thickness ($s_1$).

As shown in FIG. 2E, thinned material 30 can contact sacrificial layer 40. Moreover, as shown in FIG. 2E, thinned material 30 has a thickness ($d_3$), which can be less than about 450 Å. Further, sacrificial layer 40 has a thickness ($s_2$), which can be less than about 300 Å.

Figure 2F:
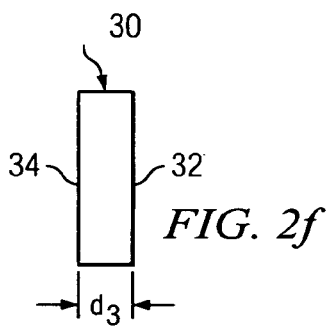

As shown in FIG. 2F, thinned material 30 can be removed from sacrificial layer 40. Thinned material 30 can be placed into a TEM and characterized. Further, site-specific TEM can be accomplished on thinned material 30 because the FIB beam allows localized and controlled milling of specific areas as opposed to bulk techniques.

According to various embodiments, thinned material 30 can be characterized by TEM even when still in contact with sacrificial layer 40. For example, thinned material 30 having thickness ($d_3$) in contact with sacrificial layer 40 having thickness ($s_2$) can be characterized by site-specific TEM. Such a configuration is shown in FIG. 2E. This can be accomplished because thinned material 30 and sacrificial layer 40 are sufficiently thin so as to permit TEM resolution.

While not intending to be limited to any particular physical theory, it is believed that sacrificial layer 40 provides improved mechanical stability to thinned material 30. For example, thinned samples are subjected to the same amount of vibrational energy as are thicker samples. However, thin samples are typically less mechanically stable than thicker samples. By adding more material, such as the sacrificial layer, the thin sample is mechanically supported. According to various embodiments, it is possible to add material so that the sample is more mechanically stable than the original sample material. Further, while not intending to be limited to any particular physical theory, it is believed that sacrificial layer 40 provides improved thermal conductivity. For example, the thinned samples are subject to a similar amount of thermal energy as are thicker samples. However, the thinned samples have a smaller volume of material. Because the thinned samples have fewer atoms with which to absorb the thermal energy, thermal distortion (either temporary or permanent) is more likely. However, by adding more material, such as the sacrificial layer, the thinned sample has more bulk with which to absorb and transport thermal energy. According to various embodiments, it is possible to add a sacrificial that is more thermally conductive than the original sample material.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of fabricating a material for transmission electron microscopy comprising:
   removing a first portion from a material having a thickness of $(d_1)$ to form a thinned material having a thickness of $(d_2)$;
   contacting one side of the thinned material to a sacrificial layer having a thickness of $(s_1)$ such that at least one side of the thinned material is exposed from the sacrificial layer; and
   removing a second portion from the exposed side of the thinned material so the thinned material has a thickness of $(d_3)$, wherein $(d_3)<(d_2)$.

2. The method of fabricating a material for transmission electron microscopy according to claim 1 further comprising:
   removing a portion of the sacrificial layer so the sacrificial layer has a thickness $(s_2)$.

3. The method of fabricating a material for transmission electron microscopy according to claim 1 further comprising:
   removing the thinned material from the sacrificial layer.

4. The method of fabricating a material for transmission electron microscopy according to claim 1, wherein the portion of the sacrificial layer is removed by at least one of a dry etch and a wet etch.

5. The method of fabricating a material for transmission electron microscopy according to claim 4, wherein the portion of the sacrificial layer is removed by at least one of focused ion beam, ion milling, and chemical etching.

6. The method of fabricating a material for transmission electron microscopy according to claim 1, wherein the first portion is removed by at least one of focused ion beam, ion milling, and chemical etching.

7. The method of fabricating a material for transmission electron microscopy according to claim 1, wherein the second portion is removed by at least one of a dry etch and a wet etch.

8. The method of fabricating a material for transmission electron microscopy comprising according to claim 1, wherein the sacrificial layer comprises at least two layers, and wherein the at least two layers are chosen from a metal layer, an insulator layer, and a semiconductor layer.

9. The method of fabricating a material for transmission electron microscopy according to claim 1, wherein $(s_1)$ is at least about 500 Å.

10. The method of fabricating a material for transmission electron microscopy according to claim 1, wherein $(s_1)$ is from about 500 Å to about 1000 Å.

11. The method of fabricating a material for transmission electron microscopy according to claim 1, wherein the sacrificial layer comprises at least one material selected from an oxide, a nitride, platinum, and glue.

12. The method of fabricating a material for transmission electron microscopy according to claim 1, wherein $(d_3)$ is less than about 450 Å.

13. The method of fabricating a material for transmission electron microscopy according to claim 1, wherein $(d_2)$ is about one half $(d_1)$.

14. A method of fabricating a thinned material for site specific transmission electron microscopy, comprising:
   removing a first portion of a first side of a material;
   contacting the first side to a sacrificial layer, wherein the sacrificial layer has a thickness of $(s_1)$;
   removing a second portion from a second side of the material; and
   removing a portion of the sacrificial layer to a thickness of $(s_2)$,
      wherein: $0 \leq (s_2) \leq (s_1)$.

15. The method of fabricating a thinned material for site specific transmission electron microscopy according to claim 14, wherein the first portion of the material is removed using a focused ion beam.

16. The method of fabricating a thinned material for site specific transmission electron microscopy according to claim 14, wherein the sacrificial layer provides structural stability and improved thermal conductivity.

17. The method of fabricating a thinned material for site specific transmission electron microscopy according to claim 14, wherein the sacrificial layer comprises at least two layers, and wherein the two layers are selected from a metal layer, an insulator layer, and a semiconductor layer.

18. The method of fabricating a thinned material for site specific transmission electron microscopy according to claim 14, wherein the portion of the sacrificial layer is removed by at least one of focused ion beam, ion milling, or chemical etching.

19. A structure for inspection using transmission electron microscopy, comprising:
   a sample material having a thickness of less than about 450 Å; and
   a sacrificial layer contacting the sample material.

20. The structure for inspection using transmission electron microscopy according to claim 19, wherein the sacrificial layer comprises at least one of an oxide, a nitride, and a metal.

21. The structure for inspection using transmission electron microscopy according to claim 19, wherein the thickness of the sample material is less than about 300 Å.

22. The structure for inspection using transmission electron microscopy according to claim 19, wherein the sacrificial layer has a thickness of $(s_2)$, and wherein: $0 \leq (s_2) \leq 1000$ Å.

23. The structure for inspection using transmission electron microscopy according to claim 19, wherein the sacrificial layer provides structural stability and improved thermal conductivity.

* * * * *